United States Patent
Chubatova et al.

(10) Patent No.: US 12,114,665 B2
(45) Date of Patent: Oct. 15, 2024

(54) BASIC COMPOSITION FOR PRODUCING A BIOLOGICALLY ACTIVE AGENT

(71) Applicants: Svetlana Alexandrovna Chubatova, Moscow (RU); Olga Igorevna Chubatova, Moscow (RU); Timofey Vyacheslavovich Petrov, Moscow (RU); Valeriy Alexeevich Mandrovskiy, Moscow (RU)

(72) Inventors: Svetlana Alexandrovna Chubatova, Moscow (RU); Olga Igorevna Chubatova, Moscow (RU); Timofey Vyacheslavovich Petrov, Moscow (RU); Valeriy Alexeevich Mandrovskiy, Moscow (RU)

(*) Notice: Subject to any disclaimer, the term of this patent is extended or adjusted under 35 U.S.C. 154(b) by 883 days.

(21) Appl. No.: 17/050,484

(22) PCT Filed: Oct. 10, 2018

(86) PCT No.: PCT/RU2018/000669
§ 371 (c)(1),
(2) Date: Oct. 26, 2020

(87) PCT Pub. No.: WO2019/209136
PCT Pub. Date: Oct. 31, 2019

(65) Prior Publication Data
US 2021/0186030 A1    Jun. 24, 2021

(30) Foreign Application Priority Data
Apr. 25, 2018    (RU) ............................ RU2018115540

(51) Int. Cl.
*A01N 65/22*    (2009.01)
*A01N 25/06*    (2006.01)
*A01N 65/12*    (2009.01)

(52) U.S. Cl.
CPC ............. *A01N 65/22* (2013.01); *A01N 25/06* (2013.01); *A01N 65/12* (2013.01)

(58) Field of Classification Search
None
See application file for complete search history.

(56) References Cited

FOREIGN PATENT DOCUMENTS

| CN | 104039338 A | * | 9/2014 | ............. | A01N 31/02 |
|---|---|---|---|---|---|
| EP | 0870507 A1 | | 10/1998 | | |
| FR | 2830198 A1 | | 4/2003 | | |
| GB | 2341091 A | * | 3/2000 | ............. | A01N 65/00 |
| JP | H111429 A | | 1/1999 | | |
| JP | 2013504553 T | | 2/2013 | | |
| KR | 100755758 B1 | | 9/2007 | | |
| KR | 1020210047069 A | | 4/2021 | | |
| KZ | 27242 A4 | | 8/2013 | | |
| RU | 2241441 C1 | | 12/2004 | | |
| RU | 2372096 C1 | | 11/2009 | | |
| RU | 2452470 C1 | | 6/2012 | | |
| WO | 9832454 A1 | | 7/1998 | | |
| WO | WO-0064265 A2 | * | 11/2000 | ............. | A01N 25/04 |
| WO | 2015138479 A1 | | 9/2015 | | |
| WO | 2017216602 A1 | | 12/2017 | | |

OTHER PUBLICATIONS

International Search Report and Written Opinion issued in International Patent Application No. PCT/RU2018/000669 dated Feb. 28, 2019 with partial English language translation (10 pages).
Zheng Jia-Qi, et al. A Discussion on Utilization of Eucalyptus in China. Eucalypt Science & Technology, vol. 34, No. 3, p. 42-46, 2017 (See translation of Office Action dated Aug. 25, 2021 from corresponding Chinese Application No. 2018800927521 for a concise explanation of the relevance of this document).
Huang Min-Fang, et al. Research Progress of Rhaponticum carthamoides. Journal of Shenyang Pharmaceutical University, vol. 25, No. 7, p. 586-592, 2008 (See translation of Office Action dated Aug. 25, 2021 from corresponding Chinese Application No. 2018800927521 for a concise explanation of the relevance of this document).
Zhang Weiming, "Aromatherapy and aromatic plants": 16 searches on duxiu.com, calendula field bactericidal essential oil, 2009, 5 pages, 2009 (See translation of Office Action dated Aug. 25, 2021 from corresponding Chinese Application No. 2018800927521 for a concise explanation of the relevance of this document).

(Continued)

*Primary Examiner* — Alton N Pryor
(74) *Attorney, Agent, or Firm* — MH2 TECHNOLOGY LAW GROUP, LLP

(57) ABSTRACT

The invention relates to biotechnology, pharmacy, cosmetology and veterinary medicine, and can be used in the manufacture of therapeutic, prophylactic, cosmetic, and sanitary and hygienic products such as sprays for air treatment, as well as gels, balms, lotions and liquids for impregnating antiseptic and immune-enhancing wipes, which do not cause side effects.

The technical problem solved by the proposed technical solution consists in increasing the aggregative stability and improving the organoleptic properties of the composition of essential oils and phytoextracts during dilution, storage, pressure increase, freezing while maintaining biological activity. The basic alcoholic-based composition for the preparation of a biologically active agent for the treatment of the human environment includes combinations of essential oils and phytoextracts at a total amount of up to 48%. Plants from the Labiatae and Compositae families rich in terpenoids, flavonoids, carotenoids and anthocyans are used as a source of essential oils and phytoextracts.

The proposed basic formulation of the composition is used to obtain agents for treating air of the indoor space by means of aerosol dispensers.

The finished products retain their biological activity during storage and use.

14 Claims, No Drawings

(56) References Cited

OTHER PUBLICATIONS

Gillian McKeith, "Food Bible", 26 searches on duxiu.com, eucalyptus basilshalfeithyme essential oil, 2008, 3 pages (See translation of Office Action dated Aug. 25, 2021 from corresponding Chinese Application No. 2018800927521 for a concise explanation of the relevance of this document).

"Encyclopedia of Aromatherapy using Essential Oils": 24 search duxiu.com, hyssop officinalis mint essential oil, 2005, 2 pages (See translation of Office Action dated Aug. 25, 2021 from corresponding Chinese Application No. 2018800927521 for a concise explanation of the relevance of this document).

Wu Wantin, "Identification and prevention of microorganisms in museums": 1331 searches on duxiu.com, bactericidal geraniol, 2016, 3 pages (See translation of Office Action dated Aug. 25, 2021 from corresponding Chinese Application No. 2018800927521 for a concise explanation of the relevance of this document).

Qian Xinzhong, "Color Illustrated Guide to Herbs of China": 209 search duxiu.com, Yarrow *Staphylococcus aureus*, 1995, 2 pages (See translation of Office Action dated Aug. 25, 2021 from corresponding Chinese Application No. 2018800927521 for a concise explanation of the relevance of this document).

Office Action dated Aug. 25, 2021 for corresponding Chinese Application No. 2018800927521, 21 pages (machine English translation).

* cited by examiner

BASIC COMPOSITION FOR PRODUCING A BIOLOGICALLY ACTIVE AGENT

CROSS-REFERENCE TO RELATED APPLICATIONS

This application is a U.S. National Stage Application of International Application No. PCT/RU2018/000669, filed on Oct. 10, 2018, which claims priority to Russian Patent Application No. 2018115540, filed on Apr. 25, 2018, the entire disclosures of which are hereby incorporated by reference in their entireties.

TECHNICAL FIELD

The invention relates to biotechnology, pharmacy, cosmetology and veterinary medicine, and can find use in the manufacture of therapeutic, prophylactic, cosmetic, and sanitary and hygienic products such as sprays for air treatment, as well as gels, balms, lotions and liquids for impregnating antiseptic and immune-enhancing wipes having no side effects.

BACKGROUND OF THE INVENTION

More than 9000 plants have medicinal properties, of which about 1500 species are known as essential-oil-bearing plants. Essential oils are a mixture of simple aliphatic and cyclic terpenoids, alcohols, ketones thereof and related benzoic acid derivatives, which can form a part of phytoextracts or are extracted in pure form. Pure essential oils have the greatest potential in the field of biomedicine. This is especially important in the context of increasing the resistance of the human body to adverse environmental factors and cleansing the air of the confined indoor space from bacteria, fungi and viruses. Multicomponent composition of essential oils provides a multilevel effect on the human body, in particular, enhances the immune response at the level of cells of the phagocytic component. The presence of various terpenes with phenolic ring and aldehydes in turn provides a widespread effect on airborne pathogens. The composition of essential oils having strong activity against microorganisms (viruses, bacteria, fungi) includes pinene, carvacrol, camphene, cineol, borneol, menthol, ocimene, camphor, limonene. Their content in certain essential oils reaches more than 30% or more than 60%. Essential oils are highly reactive and can easily penetrate the cell walls of microorganisms, disrupting their permeability, blocking the bacterial and fungal respiration, inhibiting the reproductive activity of viruses and disrupting their morphology. For example, monarda essential oil contains up to 40% thymol and up to 20% carvacrol, thus providing a bactericidal and virucidal action at a concentration of 20 to 250 μg/ml, and a fungicidal one at 100 to 200 μg/ml. The selective and concentration-dependent effect of essential oils with respect to certain types of pathogenic and opportunistic microorganisms, while being neutral at the same concentration to the bacteria of the normal flora, has been established (Nikolaevsky V. V. Aromatherapy. Spravochnik, 331 p., 2000, Vinogradova T. A., Gazhev B. N. et al. Practical herbal medicine. Great Encyclopedia, 2001, Ivashov S. V. et al. Antimicrobial activity of agents based on phytoextracts of pine, monarda, marigold for the treatment of air of indoor space of medical facilities. 2012).

However, preparations based on essential oils have not yet gained a prominent position in the sector of widely used sanitary and hygienic products. This is due to the difficulty of obtaining a stable and safe finished product due to the high degree of lability (volatility and oxidability) of essential oils and their very low solubility (0.001-0.010) in water. Essential oils are usually diluted with oil or alcoholic solvents. Oil solvents are generally acceptable in cosmetics, while alcoholic solvents are used for spraying. In both cases difficulties arise in determining the dosage. Therefore, the formulas of finished products require the preparation of complex compositions and the addition of synthetic additives and surfactants, that significantly reduces the efficiency of aromatherapy. Furthermore, the bactericidal effect, which is so important for hygiene products, is directly related to the content of terpenoids and phenolic compounds with a strong specific odor and bitter taste. This greatly hinders the use of the most efficient essential oils. However, there is a number of essential oil- and/or phytoextracts-based formulations available. Many of these formulations have a pronounced bactericidal and immune-enhancing effect.

The prior art discloses an agent based on extracts of pine, eucalyptus, sage and aspen bark for the treatment of the respiratory system, including tuberculosis (RU patent No. 2,210,379). This agent has a bitter taste and is not well tolerated by patients.

RU patent No. 2,223,108 discloses a pharmacological agent based on a composition of extracts of calendula flowers, nettle leaves, briar hips, thyme herb, melissa, oregano, ethyl alcohol, sugar, colour and water, taken in a certain ratio. The drug has a pronounced therapeutic effect (in the treatment of neurotic disorders and acute respiratory viral infections, restoring mental and physical performance, increasing the overall body resistance). The applicability of the proposed agent is limited by a long course of administration and its availability only in syrup form.

The prior art discloses a plant-based agent (RU patent No. 2,244,555) with immunomodulatory activity containing an aqueous alcoholic extract of, in parts by weight: 5.0-15.0 common licorice root, 4.0-16.0 St. John's wort herb, 4.0-16.0 dandelion root, 3.5-14.0 sandy everlasting flowers, 3.5-14.0 senna leaves, 1.0-4.0 thyme herb, 0.05-0.2 *Rhodiola rosea* rhizomes and roots, which can only be formulated as tablets or capsules.

RU patent No. 2,600,795 describes a phytocomposition in the form of a micellar solution with a prolonged action and a potent therapeutic effect. The composition contains the extracts of *eucalyptus* and *echinacea*, as well as sodium alginate or methylcellulose, a mixture of TWEEN 20 and TWEEN 80 surfactants as excipients; 96% ethyl alcohol and water contained in a certain ratio. Excipients allow ensuring stability of the composition, however, at the same time the value of the composition is reduced due to the use of surfactants which disrupt the epidermal barrier of the skin and mucous membranes.

French patent No. 2830198 discloses a composition for the treatment of viral, fungal and parasitic infections (cystic fibrosis, AIDS), comprising *Ravensara aromatica* essential oil and one or more other essential oils such as essential oils of oregano, tea tree, *Helichrysum italicum*, laurel, Ammi, elecampane, celery, *Rosmarinus officinalis, eucalyptus*, basil, lavender, thyme, St. John's wort and some plants of the citrus and myrtle family, as well as a carrier, filler or diluent. The composition has a complex and expensive formulation.

In terms of technical aspects, the closest prior art to the proposed invention is a water-alcoholic composition with an immunostimulatory, fungicidal, antimicrobial and virucidal effect, the composition comprising phytoextracts and essential oils and special additives: antioxidants and structureforming agents, wherein the ratio of the essential oils to the phytoextracts is 1:1.3, and the total concentration of the essential oils is from 0.1-0.3 to 2-3 wt. % in liposomal form (RU patent No. 2,452,470 C, IPC A61K36/15, 2011).

The disadvantage of the composition is the low aggregative stability of phytoextracts which requires a complex formulation of the special additives designed to increase its stability during storage and use. The said closest prior art uses a low concentration of essential oils and their stabilization is achieved by incorporation into liposomes, which requires an expensive technology. The stability of the liposomes, in turn, is provided by a gel structure with high water content. Such an agent freezes at low temperatures, which prevents from using it during winter, for example, in vehicles. The gel structure makes it difficult to spray this formulation in aerosol spray systems, which prevents from automation of the application process. Another disadvantage of the composition is a specific odor caused by the formulation and ratio of essential oils of the intended purpose, i.e. having antimicrobial and immunostimulatory effect.

SUMMARY OF THE INVENTION

The technical problem solved by the proposed technical solution consists in increasing the aggregative stability and improving the organoleptic properties of the composition of essential oils and phytoextracts during dilution, storage, pressure increase, freezing, while maintaining biological activity.

This problem is solved as follows. A basic composition for the preparation of a biologically active agent for the treatment of the human environment comprises essential oils, phytoextracts and an alcoholic solvent taken in a ratio of 2:1, as well as a fragrance at 1-5 wt. % of the composition, wherein the essential oils present at a total content of 20 to 32 wt. % are represented by a combination of *eucalyptus* essential oil and essential oils of plants of the Labiatae and Compositae families, and the phytoextracts are represented by a combination of extracts from pine and plants of the Labiatae and Compositae families rich in terpenoids, flavonoids, carotenoids and anthocyans. The following is used as essential oils:
  a combination of oils from plants of the Labiatae family selected from, for example: monarda, hyssop, sage, mint, lavender, basil, rosemary, oregano, thyme;
  from plants of the Compositae family selected from, for example: maral root, yarrow, marigold, wormwood, each at 2 to 14 wt. %),
  as phytoextracts, the following is used: a combination of extracts from plants of the Labiatae family, for example: sage, rosemary, thyme, motherwort, basil, skullcap, spikenard; 15
  and the Compositae family selected from, for example: calendula, dandelion, cornflower, yarrow, chamomile, burdock, *echinacea*, each independently at 1 to 12 wt. %.

Alcohols, such as ethyl alcohol, are used as the solvent.

Perfume and cosmetic compositions or aromatic essential oils are used as the fragrance.

The significant distinguishing features of the proposed technical solution are the established quantitative ratio of the composition components and the combination of the qualitative formulation of essential oils and alcoholic phytoextracts. The proposed composition is highly soluble in ethyl alcohol, can be easily introduced into the oil phase for the preparation of liposome-based agents, can be stored at various temperature conditions, has satisfactory organoleptic characteristics. The combination of light and thin essential oils (*eucalyptus*, rosemary, hyssop) with dense and viscous ones, such as chamomile, marigold and yarrow, provides a homogeneous liquid of medium fluidity.

In the extracts with a high density of 1.34 to 1.46 units, for example, of beggarticks or yarrow, the active components—flavonoids, anthocyans and resins, —can precipitate due to high content thereof. Mixing these extracts with essential oils increases the aggregative stability of the extracts, since the esters promote better dissolution of resins and flavones. On the other hand, mixing essential oils with extracts containing flavones and resins, in particular with propylene glycol ones, reduces the high degree of volatility of essential oils. Thus, mixing selected essential oils and phytoextracts in selected ratios provides the aggregative stability of the composition of essential oils and phytoextracts. The composition can contain a high content of up to 32%-34% essential oils while maintaining its stability upon freezing, pressure, dilution.

A fragrance is used in the composition to improve its organoleptic properties. In certain examples essential oils are used as the fragrance or the specially selected perfume and cosmetic compositions in the amount of 0.1 to 5.0%. The use of essential oils selected from mint, maral root, lavender improves the organoleptic properties. In the composition these oils have reduced the scent of "strong" essential oils rich in carvacrol and thymol, for example, of monarda, marigold, rosemary.

THE BEST MODE OF IMPLEMENTATION OF THE INVENTION

Examples of the formulation of the basic composition, in wt. %:

Example 1

| Essential oils: | total content | 32.0 |
| --- | --- | --- |
| eucalyptus |  | 10.0 |
| sage |  | 8.0 |
| monarda |  | 7.0 |
| hyssop |  | 5.0 |
| maral root |  | 2.0 |
| Phytoextracts: | total content | 16.0 |
| pine |  | 9.0 |
| oregano |  | 3.0 |
| echinacea |  | 2.0 |
| skullcap |  | 2.0 |
| Fragrance |  | 1.5 |
| Ethyl alcohol |  | balance |

The composition for use in aerosol dispensers with a propellant.

Example 2

| Essential oils: | total content | 30.0 |
| --- | --- | --- |
| eucalyptus |  | 14.0 |
| marigold |  | 9.0 |
| thyme |  | 3.0 |

-continued

| | | |
|---|---|---|
| oregano | | 2.0 |
| lavender | | 2.0 |
| Phytoextracts: | total content | 15.0 |
| pine | | 8.0 |
| beggarticks | | 3.0 |
| calendula | | 2.0 |
| chamomile | | 2.0 |
| Fragrance | | 2.0 |
| Isopropyl alcohol | | balance |

The composition is used in aerosol dispensers.

Example 3

| | | |
|---|---|---|
| Essential oils: | total content | 24.0 |
| eucalyptus | | 5.0 |
| thyme | | 3.0 |
| maral root | | 8.0 |
| rosemary | | 2.0 |
| lavender | | 3.0 |
| mint | | 3.0 |
| Phytoextracts: | total content | 12.0 |
| pine | | 5.0 |
| yarrow | | 2.0 |
| sage | | 2.0 |
| burdock | | 3.0 |
| Fragrance | | 4.0 |
| Ethyl alcohol | | balance |

Basic composition for preparing liposomal formulations.

Example 4

| | | |
|---|---|---|
| Essential oils: | total content | 22.0 |
| eucalyptus | | 2.0 |
| sage | | 2.0 |
| lavender | | 14.0 |
| hyssop | | 2.0 |
| basil | | 2.0 |
| Phytoextracts: | total content | 11.0 |
| pine | | 3.0 |
| motherwort | | 2.0 |
| cornflower | | 2.0 |
| spikenard | | 2.0 |
| sage | | 2.0 |
| Fragrance | | 4.0 |
| Propyl alcohol | | balance |

The composition for preparing liposomal concentrates and aerosol dispensers.

Example 5

| | | |
|---|---|---|
| Essential oils: | total content | 20.0 |
| eucalyptus | | 3.0 |
| maral root | | 5.0 |
| mint | | 3.0 |
| sage | | 5.0 |

-continued

| | | |
|---|---|---|
| oregano | | 2.0 |
| wormwood | | 2.0 |
| Phytoextracts: | total content | 10.0 |
| pine | | 4.0 |
| burdock | | 2.0 |
| yarrow | | 2.0 |
| wormwood | | 2.0 |
| Fragrance | | 3.0 |
| Ethyl alcohol | | balance |

TABLE 1

Physicochemical characteristics of the compositions

| No./No. | Stability to dilution | Stability to the addition of special additives | Density | Color | Odor characterization and assessment | |
|---|---|---|---|---|---|---|
| 1 | High 1:3:66 | 1:0.3 | 0.91 | Dark yellow | Harsh spicy | 4 |
| 2 | High 1:3 | 1:0.1 | 0.915 | Greenish yellow | Fresh, harsh | 4 |
| 3 | Medium 1:2 | 1:0.04 | 0.920 | Ocher yellow | Light grassy | 5 |
| 4 | High 1:4 | 1:0.3 | 0.900 | Yellow | Lavender | 4 |
| 5 | Medium 1:1 | 1:0.5 | 0.91 | Green | Fresh, floral | 5 |

Organoleptic characteristics were determined by performing tests on a group of volunteers among office employees (n=40 people aged from 27 to 65 years).

A score of 5 points was given to an agent that 100% of the participants liked; 4 points—to an agent that 70% of the participants liked; 3 points—to a formulation that 50% of the participants liked. As a reference product an agent TAGETON was used which has proven high bioactivity (RU U.S. Pat. No. 2,452,470—the closest prior art), which received 3 points for organoleptic characteristics (only 50% of the participants liked the smell).

Aggregative stability was determined by the resistance of the composition to the formation of turbidity or bottom precipitate, as well as stratification and other visual changes during storage, freezing, and dilution.

TABLE 2

Characterization of stability of the compositions

| Composition clarity | 1 | 2 | 3 | 4 | 5 |
|---|---|---|---|---|---|
| Initial | 0 | 0 | 0 | 0 | 0 |
| After a month/year of storage | no/change | no/change | no/change | no/change | no/change |
| After freezing | no/change | no/change | no/change | no/change | no/change |
| Dispersity when spraying | high | high | high | high | high |

TABLE 2-continued

Characterization of stability of the compositions

| Composition clarity | 1 | 2 | 3 | 4 | 5 |
|---|---|---|---|---|---|
| Color | Dark yellow | Dark yellow | Greenish yellow | Ocher yellow | Yellowy green |
| Biological activity during shelf life | +++ | +++ | +++ | +++ | +++ |

0-clear liquid according to visual assessment by three experts*.
*-the assessment is carried out in glass tubes: the inspection is conducted in daylight and a test is used (text with different fonts in the background).

The proposed basic formulation of the composition is used to obtain agents for the treatment of air of the indoor space by means of aerosol dispensers.

To obtain an agent for the treatment of air of the indoor space by means of trigger sprayers, ultrasonic humidifiers, as well as separator-type air washes, the proposed composition is used as a "premix", as a raw component in the preparation of liposomes for the finished product. The finished products retain biological activity during shelf life.

To test the antimicrobial activity of the composition in vitro (on Petri dishes), the same was converted into a water-soluble form, for example, a liposomal one, and the bacteriostatic effect was assessed using standard microbiological methods on fungi and bacteria. Table 3 provides some data obtained from the tests of the antimicrobial activity of the formulations against antibiotic-resistant bacterial strains.

TABLE 3

Antimicrobial activity of the compositions

| Strain | Source | Resistance to AMD | Formulation 1 | 2 | 3 | 4 | 5 |
|---|---|---|---|---|---|---|---|
| *Acinetobacter baumannii* B-120 | human (endotracheal aspirate) | AMC AMS CEF CTX CTA CAZ CPZ CPS PIT FEP IMI CIP CM GEN TOB AMI THR NIT | +++ | +++ | ++ | + | +/− |
| *Klebsiella pneumoniae* M-9 | environment (water) | AMP | +++ | ++ | + | ++ | − |
| *Klebsiella pneumoniae* ISV-3 | human (surgical wound) | AZR CAZ CEF NET PIT | ++ | ++ | +++ | + | +/− |
| *Pseudomonas aeruginosa* B-38/14 | human (bronchial lavage) | TCA TCC PIP PIT FEP IMI MER PEF GEN IZE TOB AMI THR CTZ MIN | + | ++ | + | − | − |
| *Pseudomonas aeruginosa* B-1957 | human (endotracheal aspirate) | IMI MER THR MIN | + | − | + | − | − |
| *Staphylococcus aureus* ATCC 25923 | human | COL | ++ | +++ | + | + | +/− |
| *Staphylococcus pasteuri* Tsarev | bird, head sinuses | COL DOC ERI TET | ++ | + | + | + | − |
| *Salmonella enterica* Lipetsk | bird, liver | TET | ++ | ++ | − | + | − |
| *Salmonella enterica* Chamzinka | bird, liver | AMC AMP DOC ERI TET TIL | ++ | + | +/− | +/− | − |

Note:
AMD—antimicrobial drugs;
AMP—ampicillin;
AMC—amoxicillin/clavulanic acid;
AMS—amoxicillin-sulbactam;
CEF—cefuroxime;
CEX - cefoxitin;
CTX—cefotaxime;
CTA, etc.—ceftriaxone;
CAZ—ceftazidime;
CPZ—cefoperazone;
TCA—ticarcillin;
TCC—ticarcillin-clavulanic acid;
CPS—cefoperazone-sulbactam;
PIP—piperacillin;
PIT—piperacillin/tazobactam;
FEP—cefepime;
ERM—ertapenem,
AZR—aztreonam;
IMI—imipenem;
MER—meropenem;
DOC—doxycycline;
TGC—tigecycline;
CIP—ciprofloxacin;
ENR—enrofloxacin;
TET—tetracycline;
PEF—pefloxacin;
CM—chloramphenicol;
GEN—gentamicin;
IZE—izepamycin;
TOB—tobramycin;
AMI—amikacin;
CTZ—co-trimoxazole;
THR—trimethoprim;
ERI—eriprim;
LIN—lincomycin;
NET—netilmicin;
PHO—phosphomycin;
NIT—nitrofurantoin;
MIN—minocycline;
COL—colistin.

The reduction of microbial contamination of the air was assessed using standard microbiological methods by taking air samples for selective media for microbial growth in the office space before and after using the agents. After the use of the agents there was a decrease in the number of microorganisms by 1.5-2.5 times per $m^3$.

The effect of the biologically active agent on human performance was determined by assessing the speed of performing work over a certain period of time using Schulte tables before using the agent and 10 minutes after using it. The tests were carried out three times (3 days in a row, at the end of the working day). In a study on a group of volunteers among 20 office employees aged from 30 to 50 years it was found that after using the agents a person spends, on average, 5.4 seconds less to perform a task than usual, when no agents based on the proposed compositions are used.

INDUSTRIAL APPLICABILITY

The invention can be used in the field of biotechnology, pharmacy, cosmetology and veterinary medicine. It can be used in the manufacture of therapeutic, prophylactic, cosmetic, and sanitary and hygienic products such as sprays for air treatment, as well as gels, balms, lotions and liquids for soaking antiseptic and immune-enhancing wipes having no side effects.

The invention claimed is:

1. A stable composition for the preparation of a biologically active agent effective in treatment of pathogens in air in an indoor space, the composition comprising essential oils and phytoextracts in a ratio of 2:1 in an alcoholic solvent, the essential oils are present at a total content of 20 to 34 wt %, based on the total weight of the stable composition, and comprising an essential oil combination of *eucalyptus* essential oil and essential oils of plants of the Labiatae and Compositae families, and a phytoextract combination of extracts from pine and plants of the Labiatae and Compositae families rich in terpenoids, flavonoids, carotenoids and anthocyans, wherein the stable composition has an antimicrobial effect or an immunostimulatory effect and further wherein the stable composition is a clear liquid, with no change in clarity of the liquid according to a visual inspection from its preparation to at least one year from its preparation.

2. The stable composition according to claim 1, wherein the essential oil combination includes one or more essential oils selected from the group consisting of monarda, hyssop, sage, mint, lavender, basil, rosemary, oregano, and thyme of the Labiatae family and maral root, yarrow, marigold, and wormwood of the Compositae family, each independently are at 2 to 14 wt %.

3. The stable composition according to claim 1, wherein the phytoextract combination includes one or more extracts selected from the group consisting of sage, rosemary, thyme, oregano, motherwort, basil, skullcap, and spikenard of the Labiatae family and calendula, dandelion, cornflower, yarrow, beggarticks, chamomile, burdock, and *echinacea* of the Compositae, each independently are at 1 to 12 wt %.

4. The stable composition according to claim 1, wherein the alcoholic solvent is selected from the group consisting of ethyl alcohol, isopropyl alcohol, and propyl alcohol.

5. The stable composition according to claim 1, further comprising a fragrance at 1-5 wt % of the composition.

6. The stable composition according to claim 5, wherein the fragrance is selected from the group consisting of perfume and cosmetic compositions and aromatic essential oils.

7. The stable composition according to claim 6, wherein the aromatic essential oils are selected from the group consisting of mint, maral root and lavender essential oils.

8. A stable composition for the preparation of a biologically active agent effective in treatment of pathogens in air in an indoor space, the composition comprising essential oils and phytoextracts in a ratio of 2:1 in an alcoholic solvent, the essential oils are present at a total content of 20 to 34 wt %, based on the total weight of the stable composition, and comprise an essential oil combination of *eucalyptus* essential oil and essential oils of plants of the Labiatae and Compositae families, and a phytoextract combination of extracts from pine and plants of the Labiatae and Compositae families rich in terpenoids, flavonoids, carotenoids and anthocyans, wherein the stable composition is a clear liquid, with no change in clarity of the liquid according to a visual inspection from its preparation to at least one year from its preparation.

9. The stable composition according to claim 8, wherein the essential oil combination includes one or more essential oils selected from the group consisting of monarda, hyssop, sage, mint, lavender, basil, rosemary, oregano, and thyme of the Labiatae family and maral root, yarrow, marigold, and wormwood of the Compositae family, each independently are at 2 to 14 wt %.

10. The stable composition according to claim 8, wherein the phytoextract combination includes one or more extracts selected from the group consisting of sage, rosemary, thyme, oregano, motherwort, basil, skullcap, and spikenard of the Labiatae family and calendula, dandelion, cornflower, yarrow, beggarticks, chamomile, burdock, and *echinacea* of the Compositae, each independently are at 1 to 12 wt %.

11. The stable composition according to claim 8, wherein the alcoholic solvent is selected from the group consisting of ethyl alcohol, isopropyl alcohol, and propyl alcohol.

12. The stable composition according to claim 8, further comprising a fragrance at 1-5 wt % of the composition.

13. The stable composition according to claim 12, wherein the fragrance is selected from the group consisting of perfume and cosmetic compositions and aromatic essential oils.

14. The stable composition according to claim 13, wherein the aromatic essential oils are selected from the group consisting of mint, maral root, and lavender essential oils.

* * * * *